(12) United States Patent
McNeil et al.

(10) Patent No.: US 10,551,368 B2
(45) Date of Patent: Feb. 4, 2020

(54) METHOD AND KIT FOR DETECTING LEAD IN A SOLID SAMPLE

(71) Applicant: THE REGENTS OF THE UNIVERSITY OF MICHIGAN, Ann Arbor, MI (US)

(72) Inventors: Anne J. McNeil, Dexter, MI (US); Kelsey N. Carter, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 146 days.

(21) Appl. No.: 15/307,021

(22) PCT Filed: May 1, 2015

(86) PCT No.: PCT/US2015/028766
§ 371 (c)(1),
(2) Date: Oct. 27, 2016

(87) PCT Pub. No.: WO2015/168533
PCT Pub. Date: Nov. 5, 2015

(65) Prior Publication Data
US 2017/0052166 A1    Feb. 23, 2017

Related U.S. Application Data

(60) Provisional application No. 61/987,786, filed on May 2, 2014.

(51) Int. Cl.
*G01N 33/20* (2019.01)
*G01N 31/22* (2006.01)

(52) U.S. Cl.
CPC ............. *G01N 33/20* (2013.01); *G01N 31/22* (2013.01)

(58) Field of Classification Search
CPC ........ G01N 33/20; G01N 31/22; G01N 21/78; G01N 21/8483; G01N 33/18; G01N 2021/752; G01N 2021/7759
See application file for complete search history.

(56) References Cited

U.S. PATENT DOCUMENTS

| 4,786,604 A | 11/1988 | Michael |
| 5,416,028 A * | 5/1995 | Stone ...................... G01N 1/34 436/164 |

(Continued)

FOREIGN PATENT DOCUMENTS

| KR | 20120053404 A | 5/2012 |
| KR | 20120097794 A | 9/2012 |

(Continued)

OTHER PUBLICATIONS

Wei et al., Novel smart supramolecular metallo-hydrogel that could selectively recognize and effectively remove Pb2+ in aqueous solution, Dec. 2012, Science China Press, vol. 55, p. 2554-2560. (Year: 2012).*

(Continued)

*Primary Examiner* — Lore R Jarrett
(74) *Attorney, Agent, or Firm* — Marshall, Gerstein & Borun LLP

(57) ABSTRACT

A method and kit for detecting the presence of lead in a solid sample is disclosed. The solid sample is brought into contact with a nonaqueous solution of a dithiocarbamate capable of forming a gel upon contact with lead, with the formation of a gel showing that lead is present in the solid sample.

10 Claims, 2 Drawing Sheets

(56) References Cited

U.S. PATENT DOCUMENTS

| | | | | |
|---|---|---|---|---|
| 5,421,897 A * | 6/1995 | Grawe | ................ | B08B 7/0014 |
| | | | | 134/6 |
| 5,494,649 A * | 2/1996 | Fristad | ..................... | B03B 5/00 |
| | | | | 423/27 |
| 5,567,619 A * | 10/1996 | Stone | ....................... | G01N 1/34 |
| | | | | 436/164 |
| 7,041,222 B1 * | 5/2006 | Rainer | .................... | C02F 1/285 |
| | | | | 210/660 |
| 2007/0110616 A1 * | 5/2007 | Blair | ..................... | G01N 31/22 |
| | | | | 422/400 |

FOREIGN PATENT DOCUMENTS

| | | |
|---|---|---|
| KR | 20120119934 A | 11/2012 |
| WO | WO-2007/055846 A1 | 5/2007 |

OTHER PUBLICATIONS

International Search Report for Patent Application No. PCT/US2015/028766, dated Jul. 24, 2015.

\* cited by examiner

METHOD AND KIT FOR DETECTING LEAD IN A SOLID SAMPLE

CROSS-REFERENCE TO RELATED APPLICATIONS

This is the U.S. national phase of International Patent Application No. PCT/US2015/028766, filed May 1, 2015, which claims the benefit of U.S. Provisional Patent Application No. 61/987,786, filed May 2, 2014, incorporated herein by reference in its entirety.

STATEMENT OF GOVERNMENTAL INTEREST

This invention was made with government support under N00014-12-1-0604 awarded by the Navy/ONR. The Government has certain rights in the invention.

FIELD OF THE INVENTION

The present invention relates to the detection of lead in a solid sample, for example, a paint chip. More particularly, the present invention relates to a method and kit for the detection of lead in a solid sample wherein gelation of a reagent solution demonstrates the presence of lead in the solid sample.

BACKGROUND OF THE INVENTION

Lead has been used for centuries in coatings, for example, as a pigment in paints, a corrosion inhibitor, and a drier in paints and varnishes. The primary reasons for using lead in coatings are properties such as durability of a finished coating, the broad spectrum of available colors using lead compounds, and corrosion, water, and weather resistance.

When lead-containing coatings age, the coatings deteriorate and consequently create lead-containing or lead-contaminated dust. Similarly, when lead-containing coatings are disturbed by cutting, drilling, sanding, or other methods commonly employed to remove building materials, lead-containing dust is released from the disturbed coating, and the dust can readily disseminate and contaminate large areas. This is a well-known public health hazard because lead-contaminated dust has been identified as a significant health hazard, particularly to children. Lead-based paints therefore were banned in 1978, but it is estimated that greater than 20 million homes may still contain lead-based coatings.

Lead contamination is not limited to paint and related products because lead has been used for decades in a wide variety of applications, such as building construction materials (roofing material, cladding, flashing, gutters and gutter joints, and on roof parapets), ammunitions, lead-acid car batteries, weights, fusible alloys, radiation shields (lead glass), and cosmetics. The use of lead in paint (wall paint, oil and water-based paint in art, paint used in toys), fuel, pipe, and plumbing material, solder for cars and pesticides has been greatly reduced over the last several decades because of the danger of lead poisoning.

Lead poisoning is a medical condition caused by increased levels of lead in the body. Exposure and accumulation to lead and lead-containing chemicals can occur through inhalation, ingestion, and/or dermal contact. Lead affects several organs in the body, and especially the nervous system. Lead also adversely effects bones (weakness in fingers, wrists, or ankles), teeth, kidneys (nephropathy and colic-like abdominal pain), the cardiovascular (blood pressure), immune, and reproductive (reduced fertility in males) systems, and can cause miscarriage in pregnant females. The adverse effects of lead on the nervous system is more pronounced in children than in adults.

Lead poisoning can be prevented by detecting lead or lead-containing compounds, and reducing or avoiding exposure to lead. To address the issue of the health risks from lead-containing dust, the United States Environmental Protection Agency (USEPA) promulgated regulations governing the appropriate methods and procedures to be used during remodeling and renovation of residential housing. These regulations stipulate that, for all housing built before 1978, the surfaces to be disturbed during renovation or remodeling must be checked for the presence of lead in the surface coatings. There are several ways lead testing can be accomplished, including Atomic Absorption spectroscopy, X-Ray Fluorescence, and chemical tests.

Atomic Absorption Spectroscopy and X-Ray Fluorescence involve sophisticated instrumentation and are expensive procedures. Several commercially-available, do-it-yourself lead test kits are available, but these kits are not quantitative and often lack credibility because they lead to false positive results. The chemical tests also often lack selectivity because test samples often contain additional compounds that can interfere with the assay for lead. Such additional compounds can include chromium, mercury, cadmium, zinc, barium, nickel, cobalt, copper, antimony, bismuth, titanium, and other metals present in pigments.

In addition, in order to achieve the different benefits of lead in various types of coatings, different forms of lead and lead-containing compounds have been incorporated into the coatings. Lead compounds that have been used in coatings include, but are not limited to lead sulfate, lead chromate, lead monoxide (litharge), lead silicate, lead sulfate blue basic, lead linoleate, lead naphthenate, and lead carbonate. While each type of lead compound has certain properties that differentiate the compound from the other lead compounds, the commonality of lead in each compound renders each compound a health risk. It is important that a detection method has the capability of detecting each type of lead compound that may be present in the solid sample. For example, some chemical assays fail to detect lead chromate.

In addition, although chemical tests to detect lead are commercially available, the tests may not properly detect lead levels at thresholds promulgated by regulatory authorities, e.g., lead equal to or exceeding 1.0 milligram per square centimeter ($mg/cm^2$) or 0.5 percent by weight (equivalent to 5,000 parts per million or ppm). In such cases, either false positive or false negative results may arise, which in the case of a false negative can lead to health issues and in the case of a false positive to unneeded and expensive remediation measures.

A need therefore still exists in the art for a fast and accurate method and test kit to detect levels of lead in a solid sample, while avoiding false positive and false negative assay results. A method and test kit that can be used by a homeowner or in the field, without the need to submit samples for testing or to require substantial user training, also is an unmet need in the art.

SUMMARY OF THE INVENTION

Figure 1:
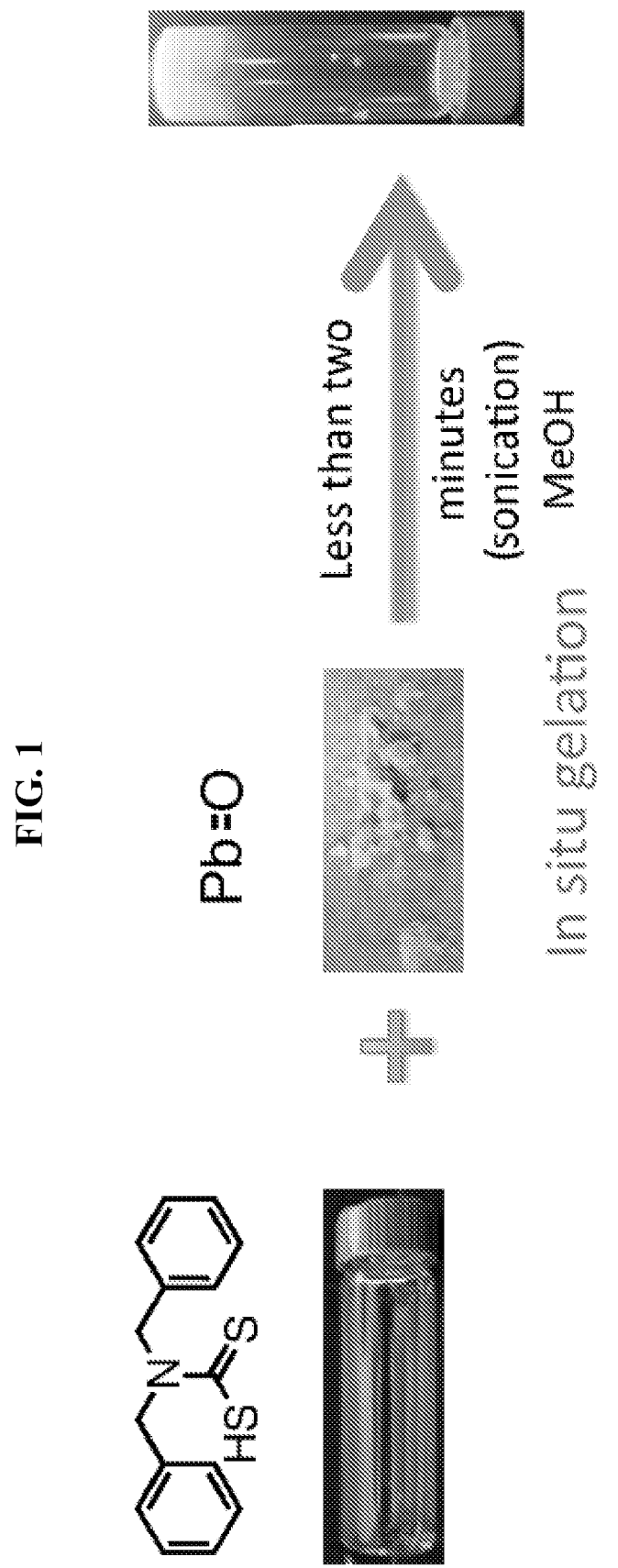
FIG. 1 illustrates the reaction which forms a gel between lead and a dithiocarbamate.

The present invention is directed to a testing kit and method of assaying a solid sample for the presence of lead. The method accurately determines the presence of lead in the solid sample without interference from other metals that may be present. In one embodiment, the kit includes (a) a dithiocarbamate compound that is capable of complexing with lead to form a gel and (b) a nonaqueous solvent. In other embodiments, the kit further contains a resealable container in which to conduct the assay.

Another aspect of the invention is to provide a method of determining the presence or absence of lead in a solid by adding a small sample of the solid to a nonaqueous solution of a dithiocarbamate capable of complexing with lead, then visually observing the resulting mixture for the formation of a gel. The dithiocarbamate is capable of complexing with additional metals, but the resulting complexes do not form a gel.

These and other aspects of the invention will become apparent from the following nonlimiting detailed description the preferred embodiments.

DETAILED DESCRIPTION OF THE PREFERRED EMBODIMENTS

Six criteria for a lead detection method have been identified. The method should be (a) capable of detecting lead concentrations of 1 mg/cm$^2$, (b) non-hazardous, (c) suitable for use as a nondestructive or minimally destructive field method, (d) suitable for use by non-technical personnel, (e) sufficiently reliable, precise, and accurate, and (f) rapid. The present invention is provides an inexpensive, more reliable lead detector that meets each of these six criteria.

The present invention provides a portable test kit to detect lead in solid samples, such as paints. The test kit contains a dithiocarbamate that gels upon binding to lead, either immediately or within a short reaction time period.

The method provides an unambiguous visual change in the physical properties/appearance of the dithiocarbamate solution upon binding to lead. The present method enables the detection of lead by naked eye with no additional instrumentation or training. The method has low critical gel concentration facilitating detection of lower analyte concentrations, i.e., as low as about 200 ppm of lead.

The present test kit can comprise a container in which the assay for lead is performed. In some embodiments, the container is optional. In this case, the individual performing the lead assay can provide a suitable container to perform the present method. The container is manufactured from a transparent material, which allows an easy visual inspection for the formation of a gel. The container therefore can be prepared from glass or a transparent plastic, such as a polycarbonate, acrylate, or urethane, for example. The shape of the container is not limited, but often is in the shape of a cylinder. The container typically has a volume of about 3 to about 25 ml, and typically, about 4 to about 10 ml, which facilitates use of the test kit in the field.

An important feature of the present method and kit is to utilize a dithiocarbamate capable of complexing with lead to form an insoluble gel in a nonaqueous solvent. Useful dithiocarbamates have a structural formula (I):

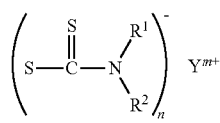

(I)

wherein n is an integer 1 or 2; m is an integer 1 or 2; $R^1$ and $R^2$, individually, are selected from the group consisting of $C_1$-$C_{10}$ linear alkyl, $C_3$-$C_{10}$ branched alkyl, $C_{2-6}$ linear alkenyl, $C_{2-6}$ branched alkenyl, $C_3$-$C_{10}$ cycloalkyl, substituted and unsubstituted aryl, and substituted and unsubstituted $(CH_2)_{1-3}$aryl, or $R^1$ and $R^2$ are taken together with the nitrogen atom to which they are attached to form a five or six membered ring, optionally fused to an aryl ring; and Y is an element selected from Groups IA and IIA of the periodic table.

In preferred embodiments, $R^1$ and $R^2$, the same or different, are substituted or unsubstituted aryl, substituted or unsubstituted $(CH_2)_{1-3}$aryl, e.g., sodium dibenzyldithiocarbamate, or $C_{2-6}$linear alkenyl, e.g., sodium diallyldithiocarbamate.

Compounds of formula (I) include, but are not limited to, sodium dimethyldithiocarbamate (CAS #128-04-1), sodium diethyldithiocarbamate (CAS #148-18-5), sodium dibenzyldithiocarbamate (CAS #55310-46-8), sodium diallyldithiocarbamate, sodium allylbenzyldithiocarbamate,

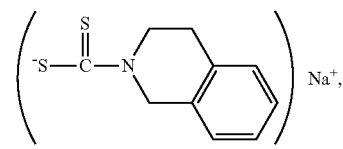

and mixtures thereof.

The dithiocarbamate is used in a sufficient amount to complex with lead in the solid sample, for example, up to the solubility limit in the nonaqueous solvent used in the assay method. Typically, the dithiocarbamate is present in a nonaqueous solvent in an amount of about 0.05 to about 5%, preferably about 0.1 to about 3%, and more preferably about 0.25 to about 1%, by weight, of the nonaqueous solution.

In addition to the dithiocarbamate, the assay method utilizes a nonaqueous solvent. The identity of the nonaqueous solvent is limited solely by an ability to solubilize the dithiocarbamate in a sufficient amount to complex with lead in a solid sample. The time required to form a lead-containing gel after contact between a solid sample and the dithiocarbamate can vary depending upon the nonaqueous solvent used in the assay. Selection of an optimum solvent, and selection of the concentration of dithiocarbamate, therefore can be readily determined by persons skilled in the art after considering the time requirements desired to obtain assay results. In preferred embodiments, the amount of water present in the nonaqueous solvent is less than 50% by volume, preferably less than 10%, by volume.

Examples of useful classes of nonaqueous solvents include, but are not limited to, alcohols, esters, glycols, glycol ethers, aliphatic and aromatic hydrocarbons, chlorinated solvents, and mixtures thereof. Specific nonlimiting examples of solvents include, but are not limited to, $C_{1-6}$alcohols, e.g., methanol, ethanol, propyl alcohol, and butyl alcohol, including isomers thereof; mono$C_{1-4}$alkyl ethers of ethylene glycol and propylene glycol; acetone; methyl ethyl ketone; isophorone; dichloromethane; chloroform; ethyl acetate; 2-methoxyethanol; DMF; DMSO; THF; acetonitrile; kerosene; mineral spirits; xylene; toluene; and mixtures thereof. Also useful are standard solvents used in the paint industry, e.g., paint thinner and turpentine.

In accordance with the present invention, a solid sample is assayed for the presence of lead by providing a reagent solution comprising a dithiocarbamate dissolved in a nonaqueous solvent. The reagent solution is placed in a transparent container and a sample of the solid is added to the solution. Alternatively, the reagent solution can be added to a transparent container containing the solid sample.

The resulting mixture optionally is shaken, then is allowed to stand uninterrupted. The container then is visually examined for the formation of a gel, as illustrated in FIG. 1. Gel formation occurs within 10 minutes, typically within 5 minutes, and usually within 2 minutes. The detection of lead in a solid sample therefore is rapid and can be performed at home or in the field.

The complexing reaction between lead and the dithiocarbamate to form a gel occurs at ambient temperature, e.g., about 20 to 30° C. To facilitate and speed gel formation, the reaction mixture can be heated above ambient temperature, for example, up to about 50° C., which temperature is limited by the identity and boiling point of the nonaqueous solvent used in the assay.

Various embodiments are envisioned for practice of the invention at home or in the field. In one embodiment, a kit comprising a ready-to-use reagent solution of a dithiocarbamate in a non-aqueous solvent in a transparent container is provided. The user then merely adds a solid test sample to the container, and the container is visually observed for a response.

In other embodiments, the kit comprises the dithiocarbamate either neat or as a concentrated solution in a nonaqueous solvent. In use, the concentrated dithiocarbamate either is added to a container contained in a kit or is added to a container provided by the user, then the user adds a sufficient amount of nonaqueous solvent to the concentrated solution to provide a reagent solution for the lead assay.

In various embodiments, the kit contains an instruction sheet for proper use of the kit, e.g., amount of solid sample to add to the reagent solution or amount and identity of solvent to add to the neat or concentrated solution of dithiocarbamate.

Example 1

In Situ Gel Formation

An 8 mL vial was charged with sodium N,N-dibenzyldithiocarbamate dissolved in methanol (0.8 mL), and the resulting mixture was heated to form a solution. A suspension of PbO in water (0.2 mL) then was added to the resulting solution. The vial was sealed, the resulting mixture was heated until homogeneous, then cooled to ambient temperature after about 20 seconds of sonication in a water bath at ambient temperature to form a gel.

In the above examples, sonication was used to speed formation of the lead-containing gel. In practical use at home or in the field, sonication is not required because the gel forms spontaneously over a slightly longer time period.

In addition to the PbO used in the examples, a lead-containing gel also forms when the solubilized dithiocarbamate forms complexes with other lead salts (e.g., $PbCra_4$, $PbCO_3$, $Pb(NO_3)_2$, and $Pb(OAc)_2$. The solubilized dithiocarbamite also forms complexes with other metals, but the resulting complex does not form a gel. The present method therefore is specific for lead.

Example 2

Figure 2:
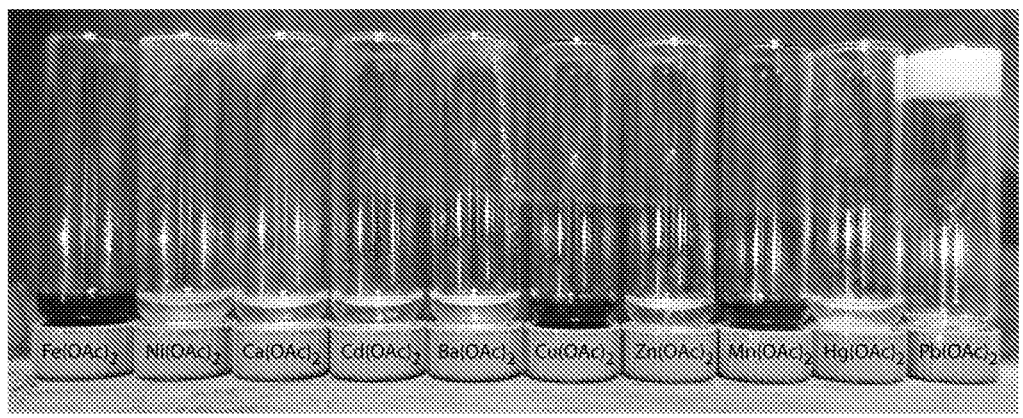
FIG. 2 illustrates the selectivity of gel formation upon contact with a lead-containing sample vs. other metal-containing sample.

To illustrate the selectivity of the present method and kit, a series of experiments was performed. In particular, an 8 mL vial was charged with sodium N,N-dibenzyldithiocarbamate (3.3 mg, 0.012 mmol) and acetone (0.5 mL), which then was shaken to dissolve the dithiocarbamate. Then, a metal acetate salt (0.006 mmol) suspended in acetone (0.5 mL) was added to the dithiocarbamate solution. The vial was capped and heated to dissolve the metal acetate salt, and the mixture then was cooled to room temperature. FIG. 2 shows that the dithiocarbamate forms a complex with a metal other than lead, but does not form a gel. The kit therefore is selective for the detection of lead.

Example 3

Figure 3:
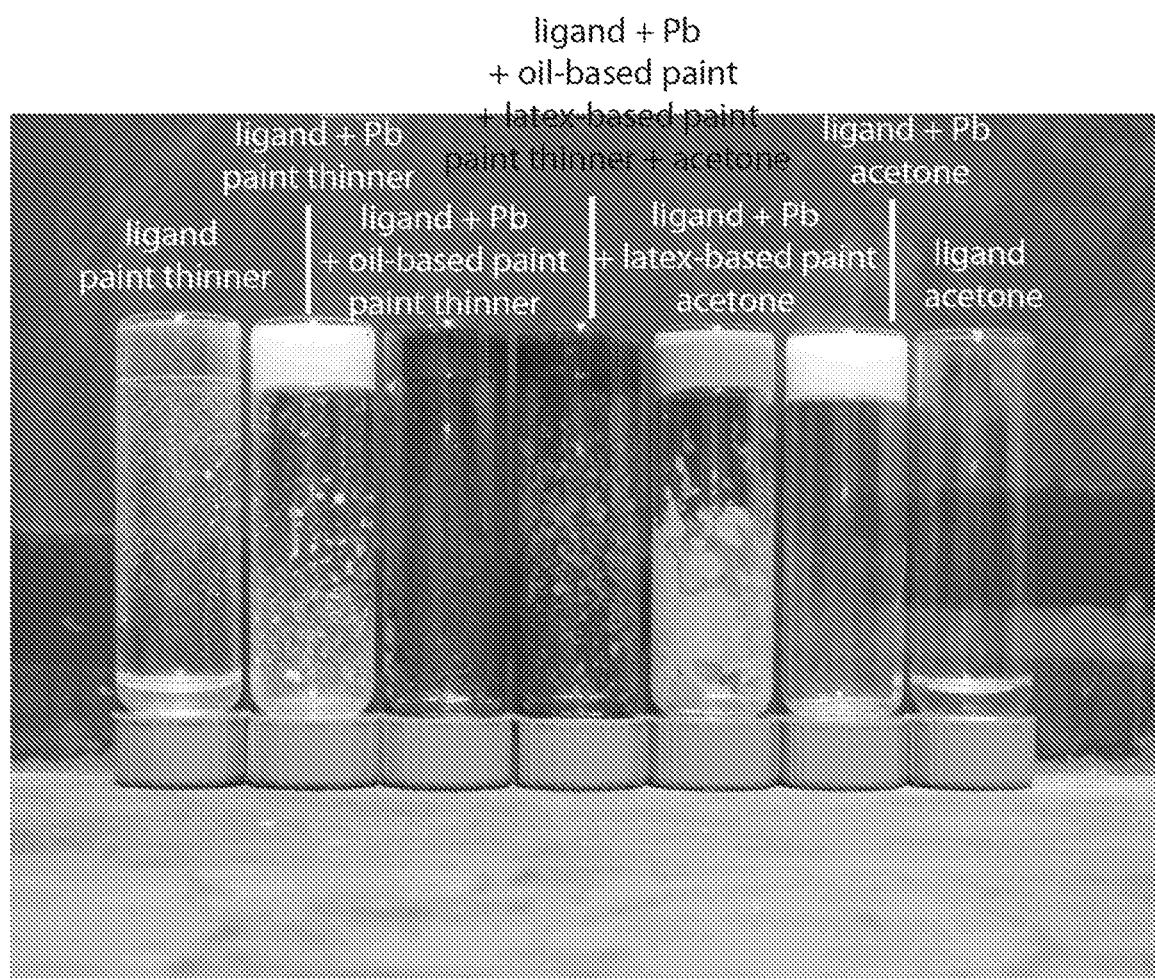
FIG. 3 illustrates various nonlimiting nonaqueous solvents used in the method of the present invention.

To illustrate that a variety of nonaqueous solvents can be used in the present method and kit, experiments were performed using a water-immiscible solvent and a water-miscible solvent were conducted. These solvents are known to dissolve latex- and oil-based paints. For example, an 8 mL vial was charged with sodium N,N-dibenzyldithiocarbamate (4.8 mg, 0.016 mmol), oil-based exterior paint (0.05 mL), and commercial paint thinner (0.5 mL). The resulting mixture was shaken to form a solution. Then, $Pb(OAc)_2$ (5.0 mg, 0.015 mmol) suspended in paint thinner (0.5 mL) was added to the solution in the vial. The vial was capped, heated to dissolve the lead salt, then cooled to room temperature to form a gel. In another example, an 8 mL vial was charged with sodium N,N-dibenzyldithiocarbamate (4.4 mg, 0.015 mmol), latex-based paint (0.05 mL), and acetone (0.5 mL). The resulting mixture was shaken to form a solution. Then, $Pb(OAc)_2$ (5.6 mg, 0.017 mmol) suspended in acetone (0.5 mL) was added to the solution in the vial. The vial was capped and heated to dissolve the lead salt, then cooled to room temperature. Upon cooling, a gel was formed. The results are illustrated in FIG. 3. The center vial of FIG. 3 shows that the present method is operative when both a latex- and oil-based paint are present in the same sample.

The present invention provides a simple to use method and a kit to assay solid samples for the presence of lead. The method and kit can be used at home or on site in the field to detect lead in paint during remodeling or renovation of older houses or buildings by general contractors and homeowners; lead in children's toys and play areas; lead in drinking water; lead in pipes, solders, and plumbing; and lead in cosmetics.

The present method and test kit provide advantages over existing assays including a simple and easy to use technology, an unambiguous detection of lead through a visible gel formation, no equipment or training to interpret test results, and an increased selectivity compared to existing lead assays.

The invention claimed is:
1. A method of determining a presence or absence of lead in a solid sample comprising:
   (a) providing a nonaqueous solution of a dithiocarbamate comprising a dibenzyldithiocarbamate, diallyldithiocarbamate, allylbenzyldithiocarbamate,

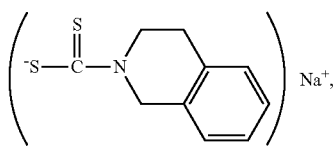

or mixtures thereof;

(b) providing a test amount of a solid sample of interest;

(c) contacting the nonaqueous solution of (a) with the solid sample test amount of (b) and observing the resulting mixture for the formation of a gel, wherein the formation of a gel indicates the presence of lead.

2. The method of claim 1 performed at a temperature of 20° C. to 50° C.

3. The method of claim 1 performed at a temperature of greater than 20° C. to 30° C.

4. The method of claim 1 wherein the nonaqueous solvent further comprises up to 50%, by volume, water.

5. The method of claim 1 wherein the solid sample contains 200 ppm or more of lead.

6. The method of claim 1, wherein the solid sample is a paint sample.

7. The method of claim 1, wherein the nonaqueous solvent comprises an alcohol, an ester, a glycol, a glycol ether, an aliphatic hydrocarbon, an aromatic hydrocarbon, a chlorinated solvent, and mixtures thereof.

8. The method of claim 1, wherein the nonaqueous solvent comprises a $C_{1-6}$ alcohols, a mono$C_{1-4}$ alkyl ether of ethylene glycol or propylene glycol, acetone, methyl ethyl ketone, isophorone, dichloromethane, chloroform, ethyl acetate, 2-methoxyethanol, DMF, DMSO, THF, acetonitrile, kerosene, mineral spirits, xylene, toluene, turpentine, paint thinner, and mixtures thereof.

9. The method of claim 1, wherein the nonaqueous solvent further comprises up to 50%, by volume, water.

10. The method of claim 1, wherein the dithiocarbonate comprises sodium dibenzyldithiocarbonate.

* * * * *